United States Patent
Matsuoka et al.

(10) Patent No.: US 8,580,904 B2
(45) Date of Patent: Nov. 12, 2013

(54) SILICONE MONOMER

(75) Inventors: Yosuke Matsuoka, Tsukuba (JP); Nobuyuki Yoshioka, Tsukuba (JP); Mao Sorimachi, Tsukuba (JP); Nobuyuki Sakamoto, Tsukuba (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 13/255,480

(22) PCT Filed: Mar. 5, 2010

(86) PCT No.: PCT/JP2010/053609
§ 371 (c)(1),
(2), (4) Date: Sep. 8, 2011

(87) PCT Pub. No.: WO2010/104000
PCT Pub. Date: Sep. 16, 2010

(65) Prior Publication Data
US 2011/0319583 A1    Dec. 29, 2011

(30) Foreign Application Priority Data
Mar. 9, 2009   (JP) ................... 2009-054796

(51) Int. Cl.
C08F 30/08   (2006.01)
C08F 16/02   (2006.01)

(52) U.S. Cl.
USPC ......................................... 526/279; 526/264

(58) Field of Classification Search
USPC ................................. 526/279, 264
See application file for complete search history.

(56) References Cited

U.S. PATENT DOCUMENTS

| | | | |
|---|---|---|---|
| 3,808,178 A | 4/1974 | Gaylord | |
| 4,139,548 A | 2/1979 | Tanaka et al. | |
| 4,260,725 A * | 4/1981 | Keogh et al. | 526/279 |
| 4,855,378 A | 8/1989 | Pradi et al. | |
| 5,371,147 A | 12/1994 | Spinelli et al. | |
| 7,084,188 B2 * | 8/2006 | Lai et al. | 523/107 |
| 2008/0000201 A1 * | 1/2008 | Schorzman et al. | 53/425 |
| 2011/0017400 A1 | 1/2011 | Dershem | |

FOREIGN PATENT DOCUMENTS

| | | |
|---|---|---|
| JP | 54-061126 A | 5/1979 |
| JP | 60-32022 A | 2/1985 |
| JP | 60032022 A * | 2/1985 |
| JP | 63-024216 A | 2/1988 |
| JP | 63-075063 A | 4/1988 |
| JP | 11-310613 A | 11/1999 |
| JP | 2008-202060 A | 9/2008 |
| WO | 2009/117729 A2 | 9/2009 |

OTHER PUBLICATIONS

Nicolson, Paul C and Jurgen Vogt. "Soft contact lens polymers:an evolution" (2001) Biomaterials 22 3273-3283.*
European Patent Office, European Search Report issued in corresponding EP Application No. 10750754.3, dated Aug. 2, 2012.

* cited by examiner

Primary Examiner — Ling Choi
Assistant Examiner — David L Miller
(74) Attorney, Agent, or Firm — Sughrue Mion, PLLC

(57) ABSTRACT

The invention provides a silicone monomer which is suitable for the manufacture of ophthalmic devices, such as contact lenses, intraocular lenses, and keratoprosthesis, a monomer composition containing the monomer, and a polymer which fulfills both surface hydrophilicity and oxygen permeability at the same time. The silicone monomer of the present invention is represented by the formula (1a) or (1b):

$$X-\underset{\substack{\|\\O}}{C}-CH_2-\underset{\substack{\|\\CH_2}}{C}-O-(CH_2)_n-\underset{\substack{|\\|\\(O-Si)_b-Z^8\\|\\Z^9}}{\overset{\substack{Z^1\\|\\(O-Si)_a-Z^2\\|\\Z^3\quad Z^4}}{Si}}-O-\underset{\substack{|\\Z^6}}{\overset{\substack{|\\Z^7}}{Si}}-Z^5 \quad (1a)$$

$$X-\underset{\substack{\|\\O}}{C}-CH_2-\underset{\substack{\|\\O}}{C}-O-(CH_2)_n-\underset{\substack{|\\|\\(O-Si)_b-Z^8\\|\\Z^9}}{\overset{\substack{Z^1\\|\\(O-Si)_a-Z^2\\|\\Z^3\quad Z^4}}{Si}}-O-\underset{\substack{|\\Z^6}}{\overset{\substack{|\\Z^7}}{Si}}-Z^5 \quad (1b)$$

(X: a monovalent C2 to C6 organic group having one or more —OH and optionally one O or N in its main chain; $Z^1$ to $Z^9$: a C1 to C4 alkyl group; n: 1 to 3; a and b: 0 or 1).

6 Claims, 5 Drawing Sheets

SILICONE MONOMER

CROSS REFERENCE TO RELATED APPLICATIONS

This application is a National Stage of International Application No. PCT/JP2010/053609 filed Mar. 5, 2010, claiming priority based on Japanese Patent Application No. 2009-054796filed Mar. 9, 2009, the contents of all of which are incorporated herein by reference in their entirety.

FIELD OF ART

The present invention relates to polymers for use in manufacture of ophthalmic devices, such as contact lenses, intraocular lenses, and keratoprosthesis; monomer compositions for use in producing the polymers; and silicone monomers for use in producing the polymers and the monomer compositions.

BACKGROUND ART

Silicone compounds such as TRIS and SiGMA represented by the formulae below are conventionally known as ophthalmic silicone monomers for use in ophthalmic devices:

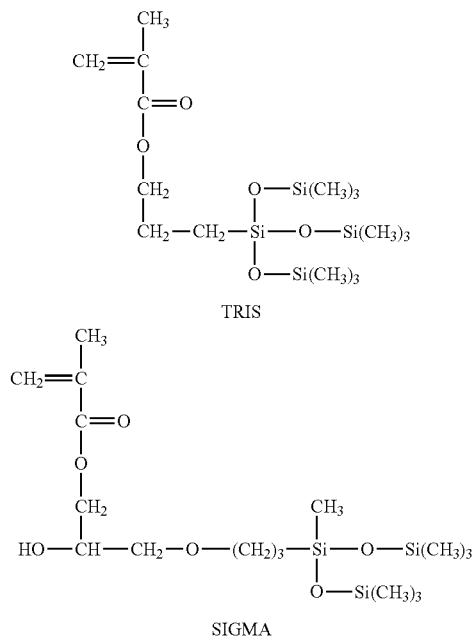

TRIS (3-[tris (trimethylsiloxy)silyl]propyl methacrylate) has been proposed for use as a material for intraocular lenses in Patent Publication 1 and Non-patent Publication 1. However, TRIS is inferior in compatibility with hydrophilic monomers, such as HEMA (2-hydroxyethyl methacrylate), and when copolymerized with such hydrophilic monomers, will not provide transparent monomers, and cannot be used as a lens material.

It is also known that combination of TRIS with other hydrophilic monomers often result in strongly water-repellent surfaces in a hydrous state, and thus inconvenient for use as a soft contact lens material.

In an attempt of overcoming these drawbacks, SiGMA ([methyl bis(trimethylsiloxy)silyl propyl]glycerol methacrylate) has been developed and used as a compatibilizing monomer for silicone hydrogel contact lenses, as disclosed in Patent Publications 2 and 3.

SiGMA also acts as an oxygen permeability formulation for its moderate oxygen permeability. SiGMA is a monomer formed readily by addition reaction of methacrylic acid and 3-glycidoxypropyl[bis(trimethylsiloxy)]methyl silane, and exhibits good hydrophilicity due to its hydroxyl group.

However, providing the percentage by mass of siloxanyl groups in one molecule of a monomer is its silicone content, the total weight of the atoms constituting the siloxanyl groups in one molecule of SiGMA is 221 and the molecular weight of SiGMA is 422, so that the silicone content of SiGMA is 221/422×100=52.4%. This means that SiGMA has a lower silicone content compared to TRIS having a 72% silicone content, which makes it difficult for SiGMA to provide sufficient oxygen permeability.

On the other hand, Patent Publication 4 proposes a novel monomer produced through the reaction of a methacrylic halide and a straight chain polyether-modified silicone. However, for giving hydrophilicity by means of polyether, the ether structural unit needs to be repeated for an increased number of times, which tends to lower the silicone content. Thus it is hard to fulfill both surface hydrophilicity and oxygen permeability of resulting lenses at the same time.

In view of the above, in the art of ophthalmic silicone monomers for use in ophthalmic devices, development of hydrophilic silicone monomers is demanded which have novel molecular structures, are easy to produce, are applicable to inexpensive uses such as daily disposable devices, and have a high percentage of siloxanyl groups (silicone content) in one molecule of the monomer.

PRIOR ART PUBLICATIONS

Patent Publications

Patent Publication 1: U.S. Pat. No. 3,808,178-A
Patent Publication 2: JP-54-61126-A
Patent Publication 3: JP-11-310613-A
Patent Publication 4: JP-2008-202060-A Non-Patent Publications Non-Patent Publication 1: Atarashii Ganka, Vol. 24(6), 2007, p 732

SUMMARY OF THE INVENTION

It is an object of the present invention to provide a polymer which has high transparency and oxygen permeability, is excellently hydrophilic, and is suitable as a material for ophthalmic devices to be applied to the eyes, as well as a monomer composition which is suitable for the production of the polymer, and has excellent homogeneity.

It is another object of the present invention to provide a silicone monomer which has a high silicone content, provides high transparency and oxygen permeability when copolymerized with a polymerizable monomer, such as a (meth)acrylic monomer, is excellently hydrophilic, and is capable of giving a polymer suitable as a material for ophthalmic devices to be applied to the eyes.

According to the present invention, there is provided a silicone monomer represented by the formula (1a) or (1b):

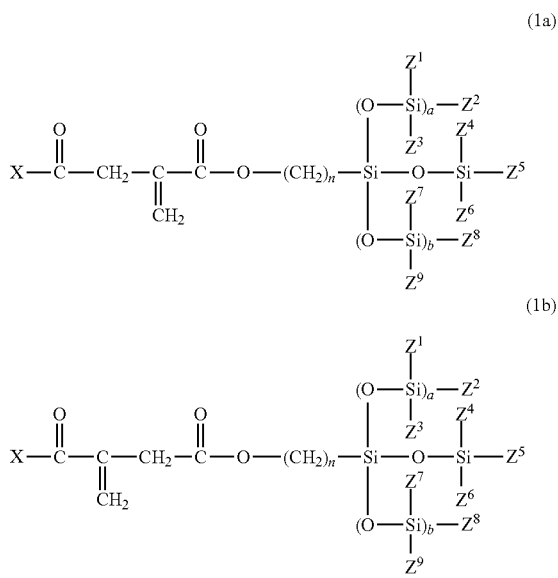

wherein X is a monovalent organic group having 2 to 6 carbon atoms and one or more hydroxyl group, and optionally one oxygen or nitrogen atom in its main chain; $Z^1$ to $Z^9$ each independently stand for an alkyl group having 1 to 4 carbon atoms; n is an integer of 1 to 3; and a and b each independently denote 0 or 1.

According to the present invention, there is also provided a monomer composition comprising at least one silicone monomer according to the present invention described above, and a hydrophilic monomer selected from the group consisting of 2-hydroxyethyl methacrylate, N-vinylpyrrolidone, N,N-dimethylacrylamide, 2-(methacryloyloxyethyl)-2-(trimethylammonioethyl)phosphate, and mixtures thereof, wherein a content of said silicone monomer of the present invention is 20 to 60 mass % of the total amount of the composition.

According to the present invention, there is also provided a polymer obtained by polymerization of the above-mentioned monomer composition.

Effect of the Invention

Having a high silicone content and a hydroxyl group, which contributes to improvement in hydrophilicity, as is seen from the formula (1a) or (1b) above, the silicone monomer of the present invention has excellent compatibility with other hydrophilic monomers, and is capable of providing a polymer which fulfills both surface hydrophilicity and oxygen permeability at the same time, when copolymerized with a polymerizable monomer, such as a (meth)acrylic monomer. Thus, the silicone monomer of the present invention is useful as a raw material monomer for the manufacture of ophthalmic devices.

Employing the silicone monomer of the present invention at a particular percentage, the polymer of the present invention has high transparency and oxygen permeability, is excellently hydrophilic, and is suitable for a material for ophthalmic devices.

Containing the silicone monomer of the present invention at a particular percentage, the monomer composition of the present invention is excellently homogeneous and useful as a raw material composition for easy production of the polymer of the present invention.

EMBODIMENTS OF THE INVENTION

Figure 1:
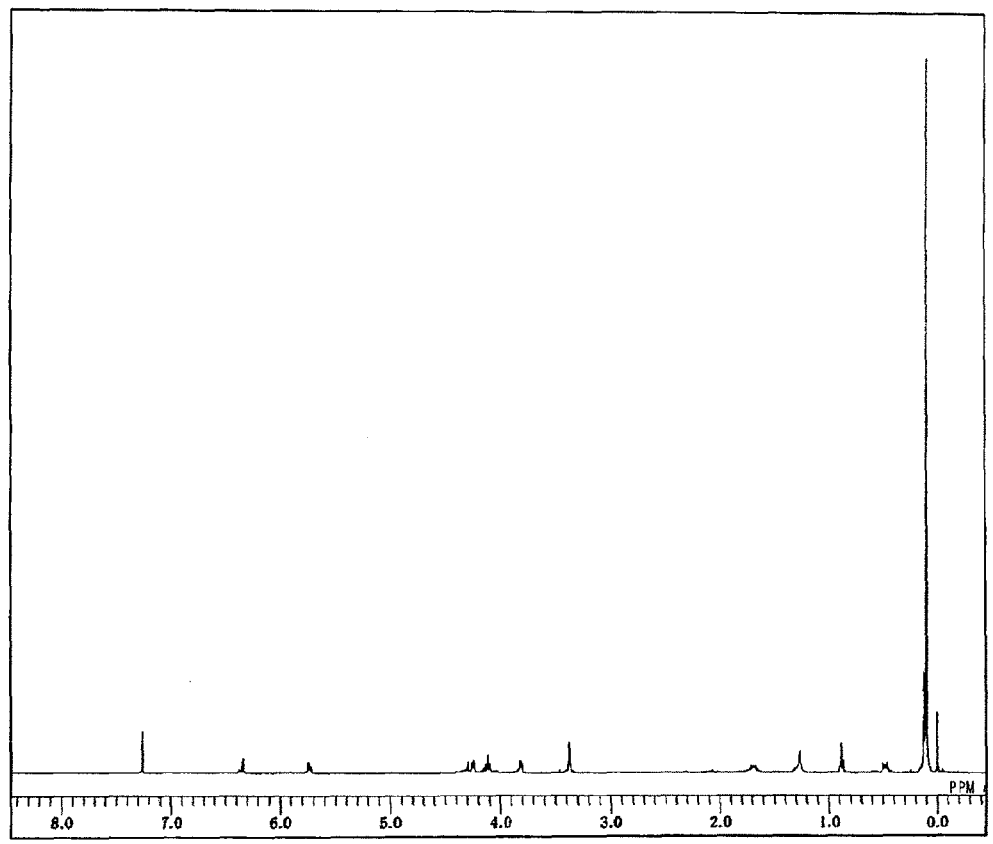
FIG. 1 is the $^1$H-NMR spectrum of the monomer synthesized in Example 1-1.

The present invention will now be explained in detail.
The silicone monomer according to the present invention is represented by the formula (1a) or (1b) described above. In the formulae (1a) and (1b), X stands for a monovalent organic group having 2 to 6 carbon atoms and one or more hydroxyl group, and optionally one oxygen or nitrogen atom in its main chain. Examples of X as a monovalent organic group may include those represented by the formula (2a) to (2f):

 (2a)

 (2b)

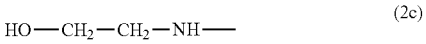 (2c)

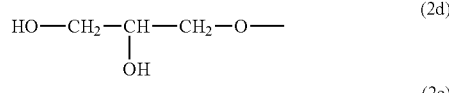 (2d)

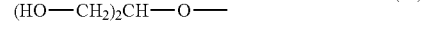 (2e)

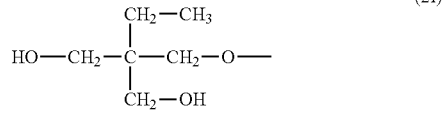 (2f)

In the formulae (1a) and (1b), $Z^1$ to $Z^9$ each independently stand for an alkyl group having 1 to 4 carbon atoms. The alkyl group may be, for example, a methyl, ethyl, n-propyl, isopropyl, n-butyl, or t-butyl group, with a methyl group being preferred for availability.

The letter n denotes an integer of 1 to 3, with 3 being preferred for availability. The letters a and b each independently stand for 0 or 1.

The silicone monomer of the present invention preferably has as high a percentage of siloxanyl groups in one molecule of the monomer as possible, and may be, for example, a compound of the formula (1a) wherein X is a group represented by the formula (2a) and a and b denote 1, such as a compound of the formula (3a), or a compound of the formula (1a) wherein X is a group represented by the formula (2c) and a and b denote 1, such as a compound of the formula (3b):

Formula (3a)

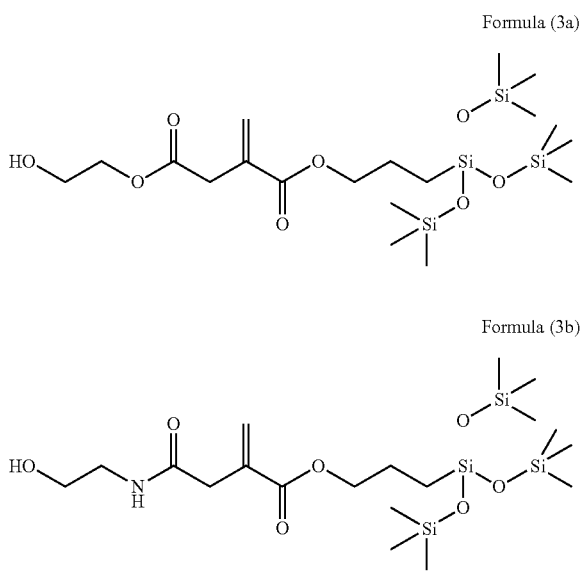

Formula (3b)

The monomer represented by the formula (3a) above has a molecular weight of 510, and the total weight of the atoms constituting the siloxanyl groups is 295, so that the monomer of the formula (3a) is a silicone monomer with a silicone content of 295/510×100=57.8%.

The monomer represented by the formula (3b) above has a molecular weight of 509, and the total weight of the atoms constituting the siloxanyl groups is 295, so that the monomer of the formula (3b) is a silicone monomer with a silicone content of 295/509×100=58.0%.

These silicone monomers have silicone contents of as high as 57% or higher, so that oxygen permeability of the resulting polymers maybe effectively improved. Among various ophthalmic devices, these silicone monomers are particularly suitable as raw material monomers for contact lenses, of which oxygen permeability is of importance.

The silicone monomer of the present invention may be obtained, for example, by reacting a carboxylic acid compound having a hydroxyl group represented by the formula (4a) or (4b) and a silicone compound represented by the formula (5):

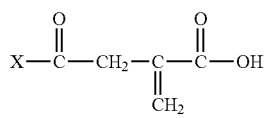 (4a)

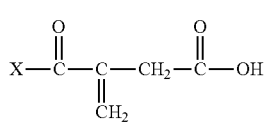 (4b)

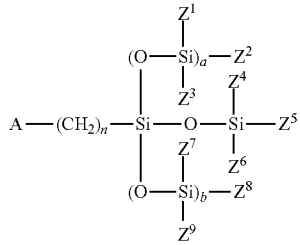 (5)

In the formulae (4a) and (4b), X stands for a monovalent organic group having 2 to 6 carbon atoms and one or more hydroxyl group, and optionally one oxygen or nitrogen atom in its main chain. Examples of X as a monovalent organic group may include those represented by the formulae (2a) to (2f) described above.

In the formula (5), A stands for halogen, preferably Br or I. $Z^1$ to $Z^9$ each independently stand for a hydrogen atom or an alkyl group having 1 to 4 carbon atoms. The alkyl group may be, for example, a methyl, ethyl, n-propyl, isopropyl, n-butyl, or t-butyl group, with a methyl group being preferred for availability. The letter n denotes an integer of 1 to 3. The letters a and b each independently stand for 0 or 1.

The reaction is preferably carried out, for example, by adding, to an organic solvent containing a 5 to 60 mass % carboxylic acid compound having a hydroxyl group represented by the formula (4a) or (4b), a silicone compound represented by the formula (5) at 10 to 100 mol % with respect to the carboxylic acid in the carboxylic acid compound having a hydroxyl group, at 20 to 80° C. in a thermostatic chamber.

The organic solvent may preferably be, for example, N,N-dimethylformamide, dimethylsulfoxide, or acetonitrile.

The reaction, which generates acid as it proceeds, is preferably carried out in the presence of a base. Preferred examples of the base may include potassium carbonate, sodium carbonate, sodium hydroxide, potassium hydroxide, triethylamine, and diazabicycloundecene, with potassium carbonate and triethylamine being more preferred.

The amount of the base to be used may preferably be 1 to 2 moles with respect to 1 mole of the silicone compound represented by the formula (5).

The carboxylic acid compound having a hydroxyl group represented by the formula (4a) or (4b) may be obtained by a conventional process. An example of a known process is reacting itaconic acid anhydride with alcohol in the presence or absence of an acid catalyst at room temperature or under heating (Journal of Organic Chemistry, 17, 116, 1952). Another example is reacting itaconic acid with an aliphatic alcohol at 70 to 100° C. in the presence of a hydrogen halide as a catalyst at not more than 2% with respect to itaconic acid to generate itaconic acid monoalkyl ester, and adding thereto an alkali/alcohol solution to neutralize and stop the reaction, thereby obtaining itaconic acid monoalkyl ester (JP-48-23721-A). These methods are known to produce predominantly a carboxylic acid compound having a hydroxyl group represented by the formula (4a).

The silicone compound represented by the formula (5) may be a commercial product, preferably a high purity product for higher purity of the resulting silicone monomer of the present invention. A high-purity silicone compound may be obtained by a conventional method as disclosed in Dokl. Akad. Nauk, SSSR, 1976, 227, 607-610, J. Organomet. Chem., 1988, 340, 31-36, or JP-2002-68930-A, for example, by reacting trialkoxysilane or trichlorosilane with hexamethyldisiloxane, followed by extraction or distillation for purification to a higher degree.

The silicone monomer according to the present invention may be used as a raw monomer material for a polymer which composes ophthalmic devices, to improve surface hydrophilicity and oxygen permeability of the devices. In order to control flexibility and the like properties of the polymer to be obtained, the present silicone monomer maybe mixed with other monomers which are copolymerizable with the present silicone monomer and usable as a material for ophthalmic devices, and used as a composition for ophthalmic devices.

The content of the silicone monomer of the present invention in the composition may suitably be decided depending on the kinds of other monomers and the like factors, and may usually be in the range of 10 to 80 mass %, and preferably in the range to be discussed later with regard to the monomer composition of the present invention.

The monomer composition according to the present invention requisitely contains a particular percentage of at least one silicone monomer of the present invention discussed above and a particular hydrophilic monomer.

The particular hydrophilic monomer is selected from the group consisting of 2-hydroxyethyl methacrylate, N-vinylpyrrolidone, N,N-dimethylacrylamide, 2-(methacryloyloxyethyl)-2-(trimethylammonioethyl) phosphate, and mixtures thereof.

In the monomer composition of the present invention, the content of the silicone monomer of the present invention is 20 to 60 masss % of the total amount of the composition. At less than 20 mass %, transparency and oxygen permeability of the polymer to be obtained by polymerization of the composition will be deteriorated, whereas at over 60 mass %, surface hydrophilicity of the polymer will be lowered.

In the monomer composition of the present invention, the content of the particular hydrophilic monomer may usually be 40 to 80 mass % of the total amount of the composition. When the composition contains other monomers to be discussed later, the content of the hydrophilic monomer maybe out of this range, e.g., 10 to 80 mass % or 20 to 80 mass %, so that the total of the monomer composition is 100 mass %.

The monomer composition of the present invention may optionally contain monomers other than the requisite monomers, which are copolymerizable with the silicone monomer of the present invention and may be used as materials for ophthalmic devices.

Such other monomers may preferably be conventional monomers having unsaturated carbon-carbon bond, such as those having a (meth)acryloyl, styryl, allyl, or vinyl group. Among these, monomers having a hydrophilic group, such as a hydroxyl, amido, or zwitterionic group, other than the particular hydrophilic monomer described above, are particularly preferred.

The content of such other monomers may usually be not more than 20 mass %, preferably not more than 10 mass % of the total amount of the composition.

The polymer according to the present invention is obtained by polymerization of the monomer composition of the present invention.

The polymerization may be carried out through a conventional method with a suitable amount of a thermal polymerization initiator, typically azo compounds, or a photopolymerization initiator.

For thermal polymerization, an initiator having suitable decomposition characteristics at a desired reaction temperature maybe selected for use. That is, peroxides or azo compounds having a ten-hour half-life temperature of 40 to 120° C. are preferred.

The photopolymerization initiator may be, for example, carbonyl compounds, sulfur compounds, halogen compounds, or metal salts.

The polymerization initiator may be used alone or in mixture, preferably at 0.5 to 2 parts by mass with respect to 100 parts by mass of the monomer composition of the present invention.

EXAMPLES

The present invention will now be explained in detail with reference to Examples, which are not intended to limit the present invention. Incidentally, the measurements in the Examples were carried out by the methods and under the conditions mentioned below.

1) Purity Measurement of Silicone Monomer (GC Method)
 Gas chromatograph: GC system 7890A manufactured by Agilent Technologies, Inc.; Capillary column: HP-1 (0.53 mm, 30 mm, 2.65 µm) manufactured by J&W; Inlet port temperature: 250° C.; Programmed temperature rise: 80° C. (0 min)→20° C./min→250° C. (20min); Detector: FID, 250° C.; Carrier gas: helium (5 ml/min) ; Split ratio: 5:1; Injection amount: 2 µl.

2) $^1$H-NMR Measurement
Measuring device: JNM-AL400 manufactured by JEOL LTD.;
Solvent: $CDCl_3$ (TMS standard)

3) Infrared (IR) Absorption Measurement
Measuring method: liquid membrane technique; Cumulated number: 16

4) Mass Measurement (LC-MS Method)
LC part: 2695 Separations Module manufactured by WATERS CORPORATION; MS part: 2695 Q-micro manufactured by WATERS CORPORATION; LC eluent conditions: acetonitrile/50 mM ammonium acetate aqueous solution (9/1).

Example 1-1

Synthesis of [tris(trimethylsiloxy)silyl]propyl=3-(2-hydroxyethoxy)carbonyl-3-butenate) (abbreviated as EitaS)

A 1 L pear-shaped flask was charged with 30.00 g of itaconic acid anhydride (0.268 moles, manufactured by TOKYO CHEMICAL INDUSTRY CO., LTD.), 33.23 g of ethylene glycol (0.536 moles), and 0.095 g of 4-methoxyphenol, and stirred at 80 ° C. for 8 hours. The reactant solution was mixed with 400 g of N,N-dimethylformamide, to which 14.80 g of potassium carbonate (0.107 moles) was added, and the solution was stirred at 50 ° C. for 30 minutes to dissolve. To the resulting solution, 49.76 g of 3-iodopropyl tris(trimethylsiloxy)silane (0.107 moles) was added dropwise, and stirred for 6 hours.

After cooling, the reactant solution was transferred to a 3 L-separating funnel, diluted with 800 g of heptane, and washed with 800 g of ion exchanged water and then with a 2% aqueous solution of sodium sulfate. Then 800 g of methanol was added to the heptane phase to extract EitaS, and then removed under reduced pressure, to thereby obtain 30.7 g of EitaS (at 56% yield). The purity of EitaS determined by GC was 92.1 mass %.

Figure 2:
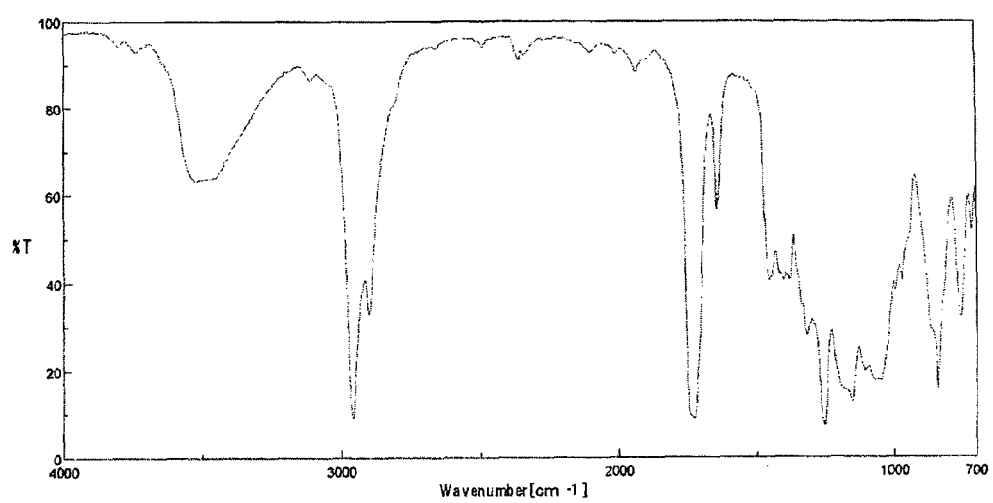
FIG. 2 is the IR spectrum of the monomer synthesized in Example 1-1.

The measured $^1$H-NMR and IR of EitaS are shown in FIGS. 1 and 2 and below:

$^1$H-NMR Measurement $CH_2=C-$: 6.35 ppm (1H), 5.73 ppm (1H); $-CH_2-$: 4.25 ppm (2H), 4.12 ppm (2H), 3.8 ppm (2H), 3.47 ppm (2H), 1.70 ppm (2H), 0.48 ppm (2H); $-CH_3$: 0.10 ppm (27H).

IR Measurement 3520 cm$^{-1}$, 2960 cm$^{-1}$, 1740 cm$^{-1}$, 1725 cm$^{-1}$, 1635 cm$^{-1}$, 1045 cm$^{-1}$, 840 cm$^{-1}$.

Structural identification of the obtained EitaS by LC-MS revealed the molecular weight of 510, from which EitaS was identified as a compound having the structure of the formula (3a) described above.

Example 1-2

Synthesis of [tris(trimethylsiloxy)silyl] propyl=3-(2-hydroxypropoxy)carbonyl-3-butenate) (abbreviated as PitaS)

A 1 L pear-shaped flask was charged with 30.00 g of itaconic acid anhydride (0.268 moles, manufactured by TOKYO CHEMICAL INDUSTRY CO., LTD.), 40.74 g of 1,3-propanediol (0.536 moles), and 0.10 g of 4-methoxyphenol, and stirred at 80° C. for 8 hours. The reactant solution was mixed with 400 g of N,N-dimethylformamide, to which 14.80 g of potassium carbonate (0.107 moles) was added, and the solution was stirred at 50° C. for 30 minutes to dissolve. To the resulting solution, 49.76 g of 3-iodopropyl tris(trimethylsiloxy)silane (0.107 moles) was added dropwise, and stirred for 6 hours.

After cooling, the reactant solution was transferred to a 3 L-separating funnel, diluted with 800 g of heptane, and washed with 800 g of ion exchanged water and then with a 2% aqueous solution of sodium sulfate. Then 800 g of methanol was added to the heptane phase to extract PitaS, and then removed under reduced pressure, to thereby obtain 34.8 g of PitaS (at 62% yield). The purity of PitaS determined by GC was 85.5 mass %.

Figure 3:
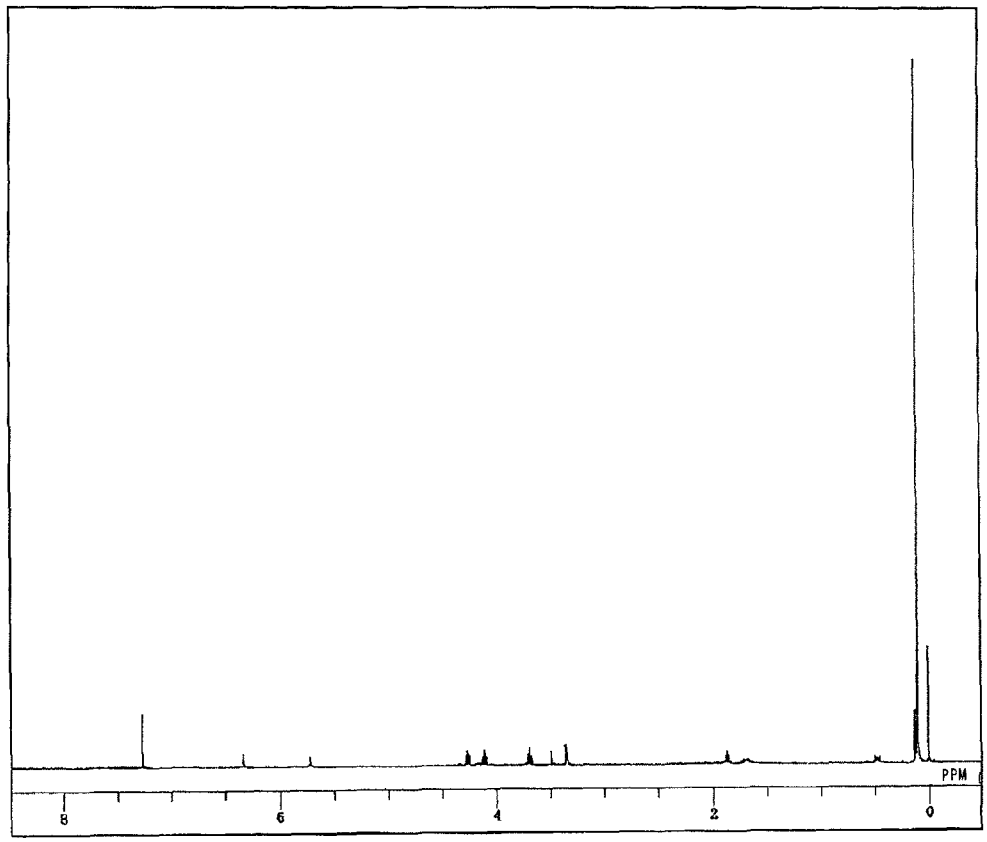
FIG. 3 is the $^1$H-NMR spectrum of the monomer synthesized in Example 1-2.
Figure 4:
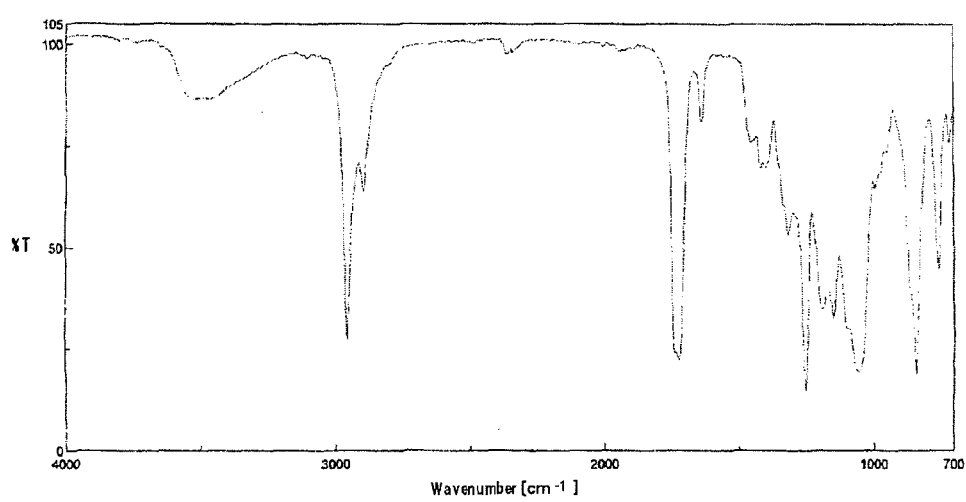
FIG. 4 is the IR spectrum of the monomer synthesized in Example 1-2.

The measured $^1$H-NMR and IR of PitaS are shown in FIGS. 3 and 4 and below:

$^1$H-NMR Measurement $CH_2=C-$: 6.35 ppm (1H), 5.73 ppm (1H); $-CH_2-$: 4.28 ppm (2H), 4.12 ppm (2H), 3.71 ppm (2H), 3.8 ppm (2H), 3.36 ppm (2H), 1.88 ppm (2H), 1.70 ppm (2H), 0.48 ppm (2H); $-CH_3$: 0.10 ppm (27H).

IR Measurement 3525 cm$^{-1}$, 2960 cm$^{-1}$, 1740 cm$^{-1}$, 1725 cm$^{-1}$, 1640 cm$^{-1}$, 1400 cm$^{-1}$, 1320 cm$^{-1}$, 1055 cm$^{-1}$, 840 cm$^{-1}$.

Structural identification of the obtained PitaS by LC-MS revealed the molecular weight of 524, from which PitaS was identified as a compound having the structure of the formula (6) below.

The silicone content of PitaS was 295/524×100=56.3%.

Formula (6)

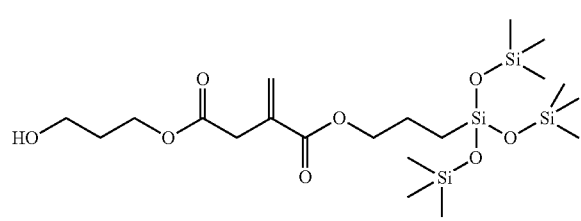

Example 1-3

Synthesis of [tris(trimethylsiloxy)silyl] propyl=3-(2,3-dihydroxypropoxy)earbonyl-3-butenate) (abbreviated as GlitaS)

A 1 L pear-shaped flask was charged with 30.00 g of itaconic acid anhydride (0.268 moles, manufactured by TOKYO CHEMICAL INDUSTRY CO., LTD.), 49.31 g of glycerin (0.536 moles), and 0.11 g of 4-methoxyphenol, and stirred at 80° C. for 8 hours. The reactant solution was mixed with 400 g of N,N-dimethylformamide, to which 14.80 g of potassium carbonate (0.107 moles) was added, and the solution was stirred at 50° C. for 30 minutes to dissolve. To the resulting solution, 49.76 g of 3-iodopropyl tris(trimethylsiloxy)silane (0.107 moles) was added dropwise, and stirred for 6 hours.

After cooling, the reactant solution was transferred to a 3 L-separating funnel, diluted with 800 g of heptane, and washed with 800 g of ion exchanged water and then twice with a 2% aqueous solution of sodium sulfate. Then 800 g of methanol was added to the heptane phase to extract GlitaS, and then removed under reduced pressure, to thereby obtain 31.3 g of GlitaS (at 54% yield). The purity of GlitaS determined by GC was 83.4 mass %.

Figure 5:
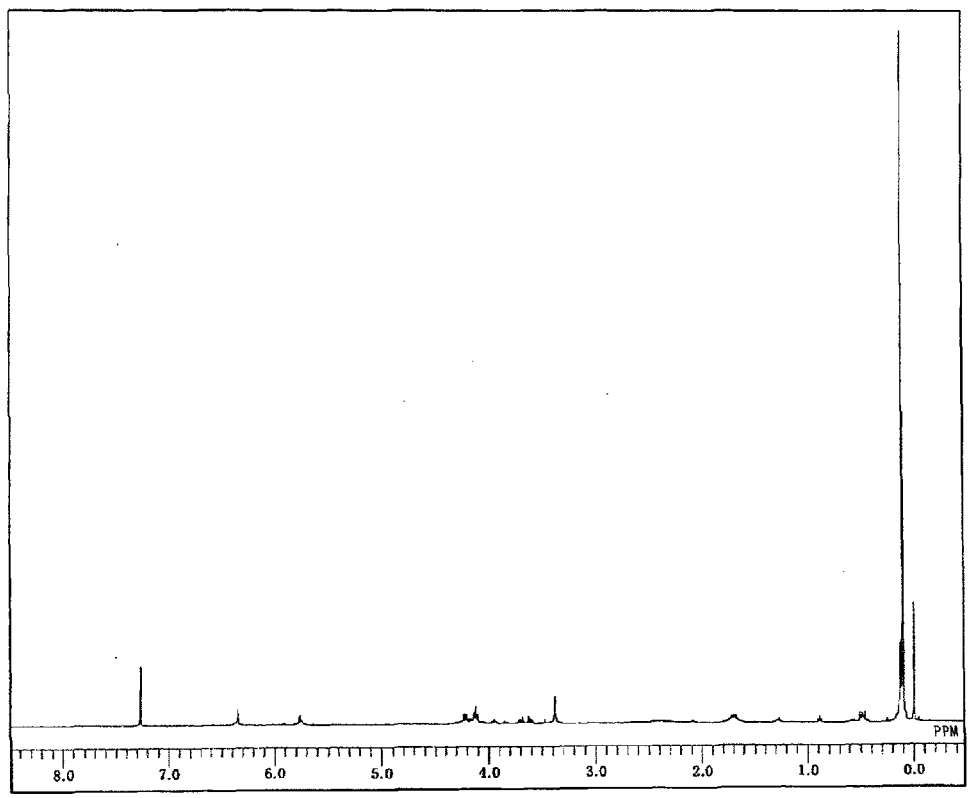
FIG. 5 is the $^1$H-NMR spectrum of the monomer synthesized in Example 1-3.
Figure 6:
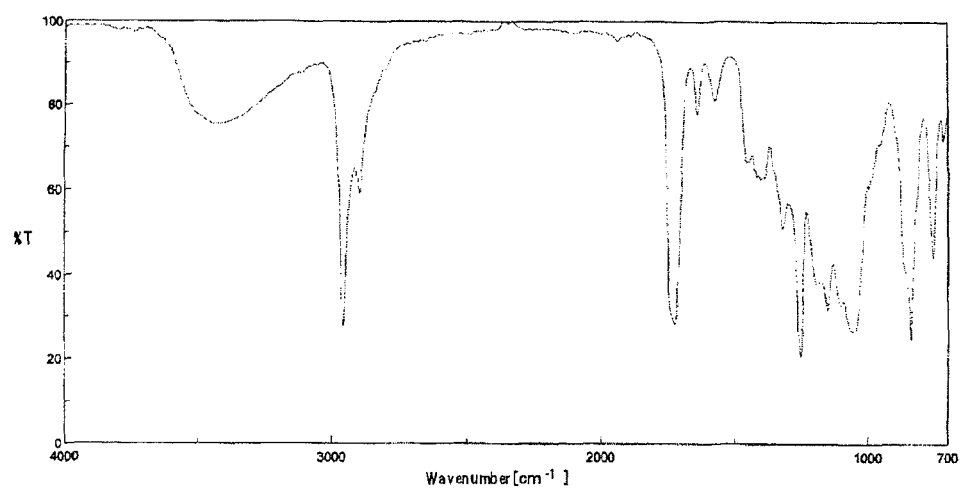
FIG. 6 is the IR spectrum of the monomer synthesized in Example 1-3.

The measured $^1$H-NMR and IR of GlitaS are shown in FIGS. 5 and 6 and below:

$^1$H-NMR Measurement $CH_2=C-$: 6.35 ppm (1H), 5.76 ppm (1H); $-CH_2-$, $-CH-$: 4.3-3.6 ppm (7H), 3.38 ppm (2H), 1.88 ppm (2H), 1.70 ppm (2H), 0.48 ppm (2H); $-CH_3$: 0.10 ppm (27H).

IR Measurement 3445 cm$^{-1}$, 2960 cm$^{-1}$, 1725 cm$^{-1}$, 1640 cm$^{-1}$, 1400 cm$^{-1}$, 1320 cm$^{-1}$, 1055 cm$^{-1}$, 840 cm$^{-1}$.

Structural identification of the obtained GlitaS by LC-MS revealed the molecular weight of 540, from which GlitaS was identified as a compound having the structure of the formula (7) below.

The silicone content of GlitaS was 295/540×100=54.6%.

Formula (7)

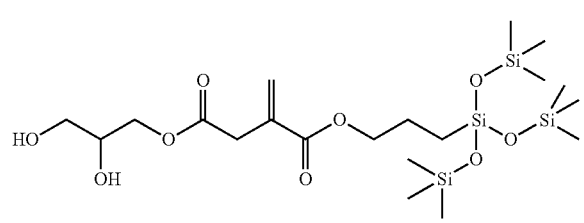

Example 1-4

Synthesis of [tris(trimethylsiloxy)silyll]propyl=3-(2,2-dihydroxymethyl)butoxycarbonyl-3- butenate (abbreviated as TrimitaS)

A 1 L pear-shaped flask was charged with 30.00 g of itaconic acid anhydride (0.268 moles, manufactured by TOKYO CHEMICAL INDUSTRY CO., LTD.), 1.84 g of trimethylolpropane (0.536 moles), and 0.132 g of 4-methoxyphenol, and stirred at 80° C. for 8 hours. The reactant solution was mixed with 400 g of N,N-dimethylformamide, to which 14.80g of potassium carbonate (0.107 moles) was added, and the solution was stirred at 50° C. for 30 minutes to dissolve. To the resulting solution, 49.76 g of 3-iodopropyl tris(trimethylsiloxy)silane (0.107 moles) was added dropwise, and stirred for 6 hours.

After cooling, the reactant solution was transferred to a 3 L-separating funnel, diluted with 800 g of heptane, and washed with 800 g of ion exchanged water and then twice with a 2% aqueous solution of sodium sulfate. Then 800 g of methanol was added to the heptane phase to extract TrimitaS, and then removed under reduced pressure, to thereby obtain 31.9 g of TrimitaS (at 51% yield). The purity of TrimitaS determined by GC was 73.5 mass %.

Figure 7:
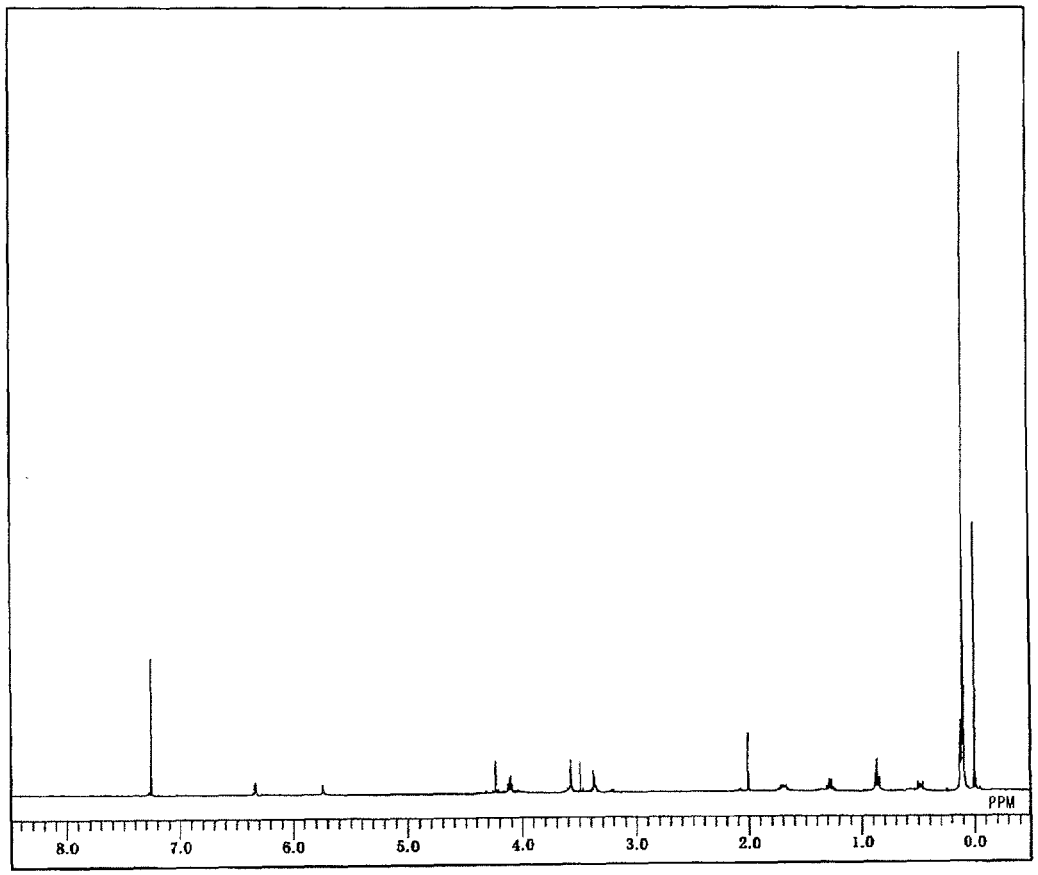
FIG. 7 is the $^1$H-NMR spectrum of the monomer synthesized in Example 1-4.
Figure 8:
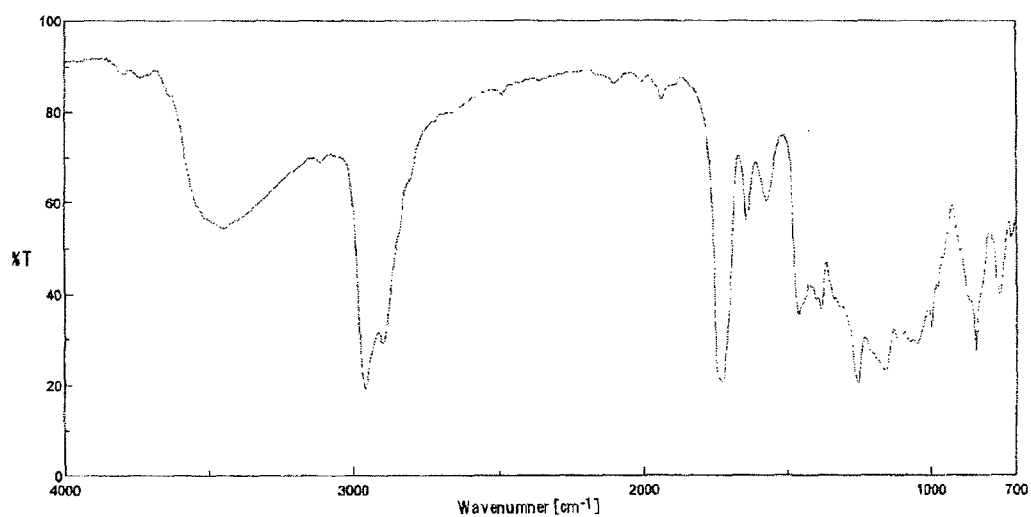
FIG. 8 is the IR spectrum of the monomer synthesized in Example 1-4.
Figure 9:
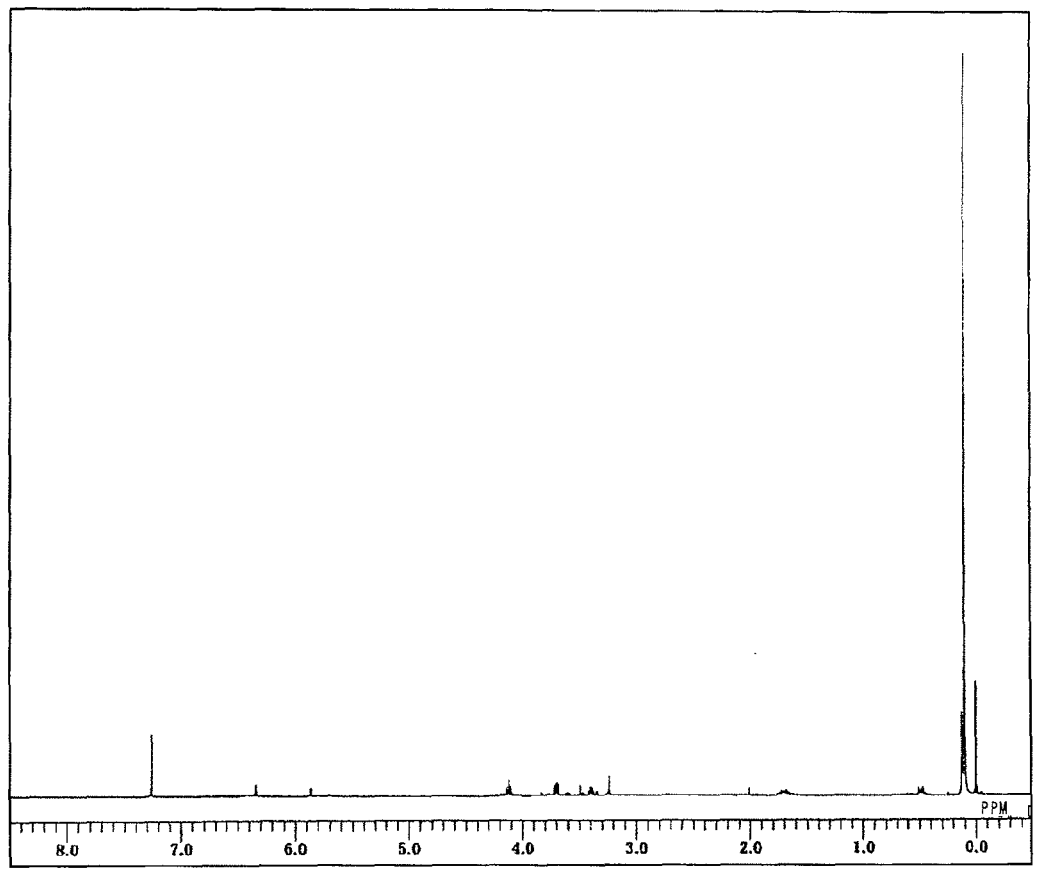
FIG. 9 is the $^1$H-NMR spectrum of the monomer synthesized in Example 1-5.

The measured $^1$H-NMR and IR of TrimitaS are shown in FIGS. 7 and 8 and below:

$^1$H-NMR Measurement $CH_2$=C—: 6.34 ppm (1H), 5.75 ppm (1H); —$CH_2$—: 4.26 ppm (3H), 4.11 ppm (2H), 3.58 ppm (3H), 3.38 ppm (2H), 1.70 ppm (2H), 0.48 ppm (2H); —$CH_3$: 0.10 ppm (27H).

IR Measurement 3445 cm$^{-1}$, 2960 cm$^{-1}$, 1725 cm$^{-1}$, 1640 cm$^{-1}$, 1460 cm$^{-1}$, 1380 cm$^{-1}$, 1045 cm$^{-1}$, 840 cm$^{-1}$.

Structural identification of the obtained TrimitaS by LC-MS revealed the molecular weight of 584, from which TrimitaS was identified as a compound having the structure of the formula (8) below.

The silicone content of TrimitaS was 295/584×100=50.5%.

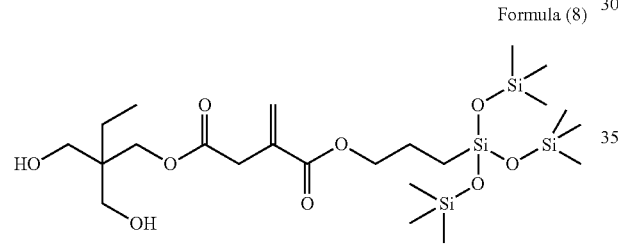

Formula (8)

Example 1-5

Synthesis of 2-[N-(2-hydroxyethyl)carbamoylmethyl]-3-[tris(trimethylsiloxy)silyl]propyl acrylate (Abbreviated as HEAmitaS)

32.70 g of 2-aminoethanol (0.536 moles) was dissolved in 65.40 g of methanol in a 1 L pear-shaped flask, and cooled. 30.00 g of itaconic acid anhydride (0.268 moles, manufactured by TOKYO CHEMICAL INDUSTRY CO., LTD.) dissolved in 30.00 g of acetone was added dropwise to the resulting solution at 0° C. over 1 hour, and stirred at room temperature for 8 hours. The solvent was removed under reduced pressure, and the reactant solution was mixed with 400 g of N,N-dimethylformamide, to which 14.80 g of potassium carbonate (0.107 moles) was added, and the solution was stirred at 50° C. for 30 minutes to dissolve. To the resulting solution, 49.76 g of 3-iodopropyl tris(trimethylsiloxy) silane (0.107 moles) was added dropwise, and stirred for 6 hours.

After cooling, the reactant solution was transferred to a 3 L-separating funnel, diluted with 800 g of heptane, and washed with 800 g of ion exchanged water and then with a 2% aqueous solution of sodium sulfate. Then 800 g of methanol was added to the heptane phase to extract HEAmitaS, and then removed under reduced pressure, to thereby obtain 30.1 g of HEAmitaS (at 54% yield). The purity of HEAmitaS determined by GC was about 60 mass %.

Figure 10:
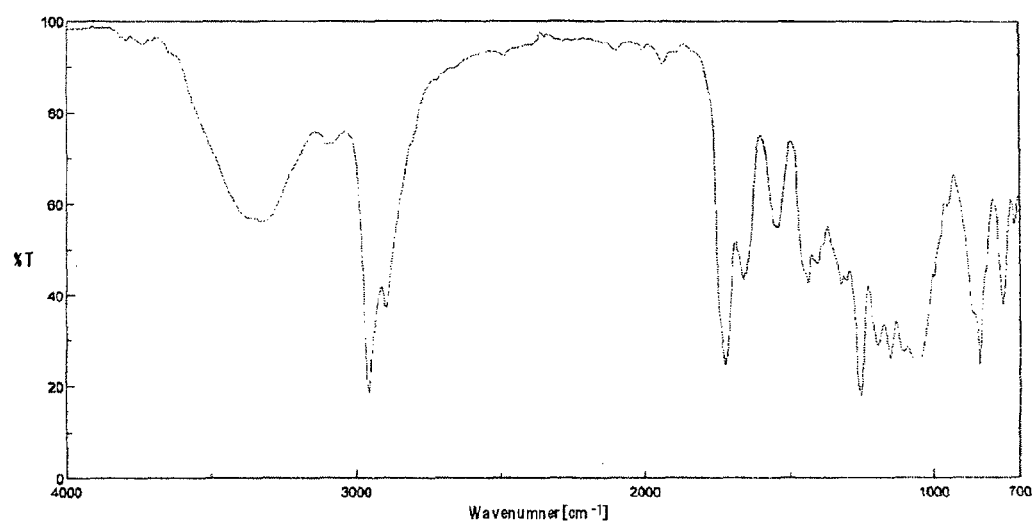
FIG. 10 is the IR spectrum of the monomer synthesized in Example 1-5.

The measured $^1$H-NMR and IR of HEAmitaS are shown in FIGS. 8 and 10 and below:

$^1$H-NMR Measurement $CH_2$=C—: 6.34 ppm (1H), 5.86 ppm (1H); —$CH_2$—: 4.11 ppm (2H), 3.71 ppm (2H), 3.37 ppm (2H), 3.24 ppm (2H), 1.70 ppm (2H), 0.49 ppm (2H); —$CH_3$: 0.10 ppm (27H); —NHC(=O)—: 6.42 ppm (1H).

IR Measurement 3320 cm$^{-1}$, 2960 cm$^{-1}$, 1725 cm$^{-1}$, 1660 cm$^{-1}$, 1550 cm$^{-1}$, 1400 cm$^{-1}$, 1320 cm$^{-1}$, 1055 cm$^{-1}$, 840 cm$^{-1}$.

Structural identification of the obtained HEAmitaS by LC-MS revealed the molecular weight of 509, from which HEAmitaS was identified as a compound having the structure of the formula (9) below.

The silicone content of HEAmitaS was 295/509×100=58.0%.

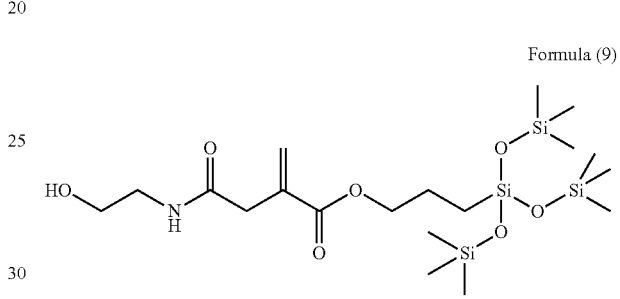

Formula (9)

Example 2-1

60 parts by mass of 2-hydroxyethylmethacrylate (abbreviated as HEMA), 40 parts by mass of EitaS represented by the formula (3a), 0.5 parts by mass of ethylene glycol dimethacrylate (abbreviated as EDMA), and 0.5 parts by mass of α,α'-azobisisobutyronitrile (abbreviated as AIBN) were mixed and dissolved homogeneously. The obtained mixture was poured into a cell, which had been fabricated of polypropylene plates holding a 1 mm thick polyethylene terephthalate sheet therebetween as a spacer, and left to stand in an oven swept with nitrogen at 100° C. for 2 hours, to thereby obtain a polymer. The obtained polymer was immersed in physiological saline as described in ISO 18369-3 to swell into a transparent polymer gel.

The obtained polymer and the mixture before the polymerization were subjected to the following evaluations. The results are shown in Table 1.

[Evaluation of Homogeneity of Unpolymerized Mixture]

The unpolymerized mixture was placed in a colorless, transparent vessel, and visually observed whether it is clear, white-turbid, or precipitated.

[Evaluation of Transparency of Polymer]

The swollen polymer gel was visually observed for transparency, i.e., whether it was transparent, slightly turbid, or white turbid.

[Evaluation of Surface Wettability]

The swollen polymer gel was taken out of the physiological saline, and the time required for the water film on the surface of the gel to rupture was measured. The gel was evaluated as acceptable when the water film was ruptured after 30 seconds or later, and unacceptable when the water film was ruptured within less than 30 seconds.

[Measurement of Oxygen Permeability]

The oxygen permeability coefficient (Dk) was determined according to the method defined in ISO 9913-1 (FATT method) using an oxygen permeability meter (K-316, manufactured by TSUKUBA RIKA SEIKI CO., LTD.).

Examples 2-2 to 2-10

Transparent polymer gels were obtained through polymerization in the same way as in Example 2-1 except that the compositional ratios of the monomers and other components were changed as shown in Table 1, followed by immersion in physiological saline as defined in ISO 18369-3. The evaluations were made in the same way as in Example 2-1. The results are shown in Table 1. Incidentally, Dk was not determined for the gels prepared in Examples 2-4, 2-7, and 2-10.

The term MPC in Table 1 stands for 2-(methacryloyloxyethyl)-2-(trimethylammonioethyl)phosphate.

Comparative Example 1

30 parts by mass of HEMA, 70 parts by mass of EitaS, 0.5 parts by mass of EDMA, and 0.5 parts by mass of AIBN were mixed and dissolved homogeneously. The obtained mixture was poured into a cell, which had been fabricated of polypropylene plates holding a 1 mm thick polyethylene terephthalate sheet therebetween as a spacer, and left to stand in an oven swept with nitrogen at 100° C. for 2 hours, to thereby obtain a polymer. The obtained polymer was immersed in physiological saline as described in ISO 18369-3 to swell into a transparent polymer gel. The evaluations except for Dk were made in the same way as in Example 2-1. The results are shown in Table 1. It was found that the obtained polymer did not have sufficient surface hydrophilicity.

Comparative Example 2

90 parts by mass of N-vinylpyrrolidone (abbreviated as Vp), 10 parts by mass of EitaS, 0.5 parts by mass of EDMA, and 0.5 parts by mass of AIBN were mixed and dissolved homogeneously. The obtained mixture was poured into a cell, which had been fabricated of polypropylene plates holding a 1 mm thick polyethylene terephthalate sheet therebetween as a spacer, and left to stand in an oven swept with nitrogen at 100° C. for 2 hours, to thereby obtain a polymer. The obtained polymer was immersed in physiological saline as described in ISO 18369-3 to swell. The evaluations other than Dk were made in the same way as in Example 2-1. The results are shown in Table 1. The obtained polymer gel was white turbid, and did not have sufficient surface hydrophilicity.

Comparative Example 3

A polymer gel was obtained through polymerization in the same way as in Example 2-1 except that EitaS was replaced with 3-[tris(trimethylsiloxy)silyl]propyl methacrylate (TRIS), followed by immersion in physiological saline as defined in ISO 18369-3. The evaluations except for the surface wettability and Dk were made in the same way as in Example 2-1. The results are shown in Table 1. The obtained polymer gel was white turbid.

Comparative Example 4

The monomers and other components were mixed in the same way as in Example 2-6 except that EitaS was replaced with TRIS, but did not dissolve homogeneously. The compositional ratio of the monomers and other components and the result of the homogeneity evaluation of the unpolymerized mixture are shown in Table 1.

TABLE 1

| | | Example | | | | | | | |
|---|---|---|---|---|---|---|---|---|---|
| | | 2-1 | 2-2 | 2-3 | 2-4 | 2-5 | 2-6 | 2-7 | 2-8 |
| Materials | EitaS | 40 | 50 | 60 | 20 | 40 | 40 | 40 | 60 |
| | TRIS | | | | | | | | |
| | MPC | | | | | | 10 | 15 | 10 |
| | HEMA | 60 | 20 | | 40 | 30 | 25 | 45 | 10 |
| | Vp | | 30 | 40 | 40 | 30 | 25 | | |
| | DMA | | | | | | | | 20 |
| | EDMA | 0.5 | 0.5 | 0.5 | 0.5 | 0.5 | 0.5 | 0.5 | 0.5 |
| | AIBN | 0.5 | 0.5 | 0.5 | 0.5 | 0.5 | 0.5 | 0.5 | 0.5 |
| Evaluation | Homogeneity of mixture | Clear | Clear | Clear | Clear | Clear | Clear | Clear | Clear |
| | Transparency of polymer | Transparent | Transparent | Transparent | Transparent | Transparent | Transparent | Transparent | Transparent |
| | Surface wettability | Acceptable | Acceptable | Acceptable | Acceptable | Acceptable | Acceptable | Acceptable | Acceptable |
| | Oxygen permeability (Dk) | 85 | 95 | 80 | — | 94 | 91 | — | 64 |

| | | Example | | Comparative Example | | | |
|---|---|---|---|---|---|---|---|
| | | 2-9 | 2-10 | 1 | 2 | 3 | 4 |
| Materials | EitaS | 60 | 60 | 70 | 10 | | |
| | TRIS | | | | | 40 | 40 |
| | MPC | 10 | 15 | | | | 10 |
| | HEMA | 10 | 10 | 30 | 90 | 60 | 25 |
| | Vp | 20 | | | | | 25 |
| | DMA | | 15 | | | | |
| | EDMA | 0.5 | 0.5 | 0.5 | 0.5 | 0.5 | 0.5 |
| | AIBN | 0.5 | 0.5 | 0.5 | 0.5 | 0.5 | 0.5 |

TABLE 1-continued

| Evaluation | Homogeneity of mixture | Clear | Clear | Clear | Clear | Clear | White turbid |
|---|---|---|---|---|---|---|---|
| | Transparency of polymer | Transparent | Transparent | Transparent | White turbid | White turbid | — |
| | Surface wettability | Acceptable | Acceptable | Unacceptable | Unacceptable | — | — |
| | Oxygen permeability (Dk) | 106 | — | — | — | — | — |

EitaS: Compound represented by formula (3a)
TRIS: tris(trimethylsiloxy)silyl]propyl methacrylate
MPC: 2-(methacryloyloxyethyl)-2-(trimethylammonioethyl) phosphate
HEMA: 2-hydroxyethyl methacrylate
Vp: N-vinylpyrrolidone
DMA: N,N-dimethylacrylamide
EDMA: ethylene glycol dimethacrylate
AIBN: α,α'-azobisisobutyronitrile

INDUSTRIAL APPLICABILITY

The silicone monomer and the monomer composition according to the present invention may suitably be used as raw materials for ophthalmic devices, in particular contact lenses, and are highly industrially useful as novel materials. The polymer of the present invention is suitable as a material for ophthalmic devices, in particular contact lenses.

What is claimed is:

1. A silicone monomer represented by the formula (1a) or (1b):

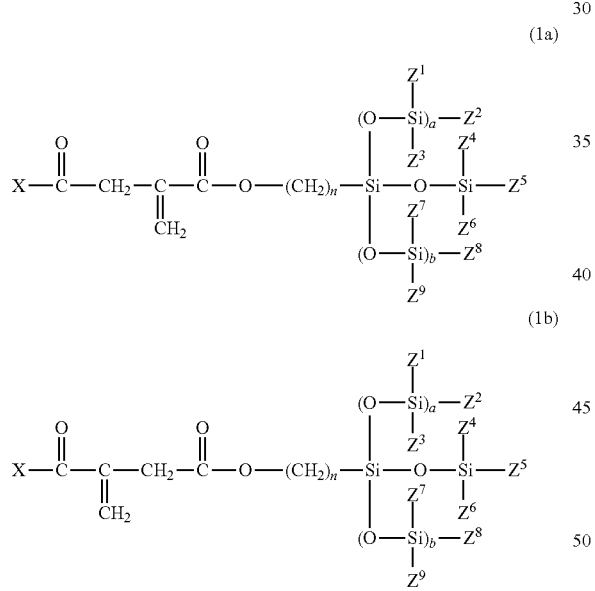

wherein X is a monovalent organic group having 2 to 6 carbon atoms and one or more hydroxyl group, and optionally one oxygen or nitrogen atom in its main chain; $Z^1$ to $Z^9$ each independently stand for an alkyl group having 1 to 4 carbon atoms; n is an integer of 1 to 3; and a and b each independently denote 0 or 1.

2. The silicone monomer of claim 1, wherein X is selected from the groups represented by formulae (2a) to (2f):

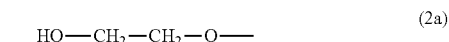
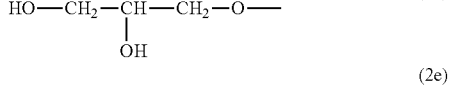
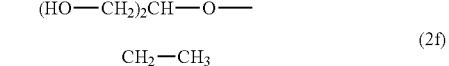

3. A monomer composition comprising:
at least one silicone monomer according to claim 1, and
a hydrophilic monomer selected from the group consisting of 2-hydroxyethyl methacrylate, N-vinylpyrrolidone, N,N-dimethylacrylamide, 2-(methacryloyloxyethyl)-2-(trimethylammonioethyl) phosphate, and mixtures thereof,
wherein the content of said silicone monomer is 20 to 60 mass % of a total amount of said composition.

4. A polymer obtained by polymerization of a monomer composition according to claim 3.

5. A monomer composition comprising:
at least one silicone monomer according to claim 2, and
a hydrophilic monomer selected from the group consisting of 2-hydroxyethyl methacrylate, N-vinylpyrrolidone, N,N-dimethylacrylamide, 2-(methacryloyloxyethyl)-2-(trimethylammonioethyl) phosphate, and mixtures thereof,
wherein the content of said silicone monomer is 20 to 60 mass % of a total amount of said composition.

6. A polymer obtained by polymerization of a monomer composition according to claim 5.

* * * * *